United States Patent
Yu et al.

[11] 4,034,114
[45] July 5, 1977

[54] TREATMENT OF SKIN KERATOSES WITH RETINAL

[76] Inventors: Ruey J. Yu, 4400 Dexter St., Philadelphia, Pa. 19128; Eugene J. Van Scott, 1138 Sewell Lane, Rydal, Pa. 19046

[22] Filed: Sept. 15, 1976

[21] Appl. No.: 723,327

[52] U.S. Cl. .............................. 424/333; 424/318; 424/344
[51] Int. Cl.$^2$ ...................................... A61K 31/11
[58] Field of Search .................. 424/233, 318, 344

[56] References Cited
UNITED STATES PATENTS

| | | | |
|---|---|---|---|
| 3,729,568 | 4/1973 | Kligman | 424/318 |
| 3,932,665 | 1/1976 | Van Scott et al. | 424/333 |

FOREIGN PATENTS OR APPLICATIONS

| | | | |
|---|---|---|---|
| 902,659 | 7/1962 | United Kingdom | 424/344 |

*Primary Examiner*—Norman A. Drezin
*Attorney, Agent, or Firm*—LeBlanc & Shur

[57] ABSTRACT

A treatment to alleviate the symptoms of actinic or nonactinic keratoses consisting of topical application of a solution, lotion, cream or ointment containing retinal is disclosed. The therapeutic composition may include retinal as an active ingredient present in an amount of from 0.01 to 2 percent by weight of the total composition. Topical application of the therapeutic composition in a solution, lotion, cream or ointment has been found to achieve from substantial to complete remissions of the keratoses in humans.

8 Claims, No Drawings

TREATMENT OF SKIN KERATOSES WITH RETINAL

Keratoses of the skin may be classified into two groups, namely actinic and nonactinic keratoses. Actinic keratoses, also known as solar or senile keratoses, are found most commonly in Caucasians with fair colored skin, and almost exclusively in persons with poor ability to tan. Development of actinic keratoses is quite common among people who live in sunny climates such as Australia or the southern United States.

Lesions of actinic keratoses are found only in the sunlight exposed areas of the body such as on the face. The clinical lesion frequently consists of a scaly plaque usually less than 1 cm in diameter with freckled pigmentation varying from yellow, brown to blackish depending on the amount of adherent horny material. In addition, there is usually a pinkish tinge of the entire lesion or a red periphery. Without any treatment actinic keratoses may take one of three courses: (a) disappear spontaneously, (b) stay the same, (c) evolve into epidermal carcinoma.

The nonactinic keratoses may be caused by X-ray, radium or chemical carcinogens such as arsenic compounds, or may arise without evident cause. The clinical features of nonactinic keratoses are the same as that of actinic keratoses except that localizations of lesions are not restricted to sunlight exposed areas of the skin.

Common treatments for actinic or nonactinic keratoses (hereinafter referred to as keratoses) are either surgical removal of the lesions or topical administration of 5-fluorouracil. Since surgical management has its limitations due to clinical conditions such as number and size of lesions and also cosmetic disfigurements, topical treatment is still a common and desirable approach.

Current use of 1 to 5% 5-fluorouracil for topical treatment of the aforementioned keratoses is effective in eradicating the lesions. However, use of 5-fluorouracil has the following shortcomings. When this compound is used for topical treatment of the keratoses erythema always develops after 3 or 4 days of twice-daily application, and a inflammatory response follows that is roughly proportional to the amount of skin damage. Discomfort and local tenderness are common, and pain and ulceration frequently occur. The peak response occurs 2 weeks after treatment is started, and there may be unsightly and extensive soft tissue swelling. In addition to the aforementioned pain and discomfort the patient must suffer during the topical treatment with 5-fluorouracil, allergic sensitization to this compound has been found to occur in about 1% of the patients treated.

Topical treatment of the keratoses with 5-fluorouracil has been considered to be safe and devoid of internal toxic side effects. However, it is well documented that 5-fluorouracil when given systemically to humans induces delayed-type, clinical toxicity. The earliest toxic symptoms are anorexia and nausea; these are followed shortly after by stomatitis and diarrhea. Stomatitis may be preceded by a sensation of dryness, followed by erythema and formation of a white, patchy membrane that develops into ulceration and necrosis. The major toxic effects, however, result from the myelosuppressive action of this drug; clinically manifested as leukopenia. Thrombocytopenia and anemia may follow. Loss of hair, occasionally progressing to total alopecia, nail changes, dermatitis, and atrophy of the skin may be encountered. Neurological toxic symptoms have been reported, and myelopathy has been found after systemic administration of this drug.

A recent article by Bollag and Ott in *Cancer Chemotherapy Reports*, Volume 55, p. 59 (1971), indicated that patients with actinic keratoses had been successfully treated with topical administration of retinoic acid (Vitamin A acid). The treatment included the topical application of either 0.1 to 0.3% active ingredient in a fatty ointment. Fifty-one out of sixty patients treated with the above ointment containing retinoic acid showed substantial improvement or complete remission of the keratotic lesions on face, hands and forearms. However, topical treatment with retinoic acid was always accompanied by a severe inflammatory reaction with redness and occasional exudation. Bollag and Ott therefore concluded that topical treatment of actinic keratoses with retinoic acid was not recommended for practical routine therapy.

It is therefore desirable to develop other efficacious drugs, preferably of physiologic origin, which do not cause irritation, pain, allergic reaction or systemic toxicity during or after topic treatment of the keratoses.

Retinal, $C_{20}H_{28}O$, also known as vitamin A aldehyde is a chemical substance of physiologic origin in animals and humans. One of the most important roles retinal plays in animals and humans is in visual function. Deficiency of retinal in the retina of the eye always leads to so-called "Night Blindness." In addition to its role in visual function retinal provides essential vitamin A required for normal growth, for maintenance of normal reproduction performance and for normal differentiation of epithelial tissues.

In our U.S. Pat. No. 3,932,665, which issued Jan. 13, 1976, retinal was described and claimed as a therapeutic agent in a method for treating acne by topical application. The disclosure of the aformentioned U.S. Pat. No. 3,932,665 is accordingly hereby incorporated by reference. However, that patent described our discovery that regular topical applications of a retinal-containing composition promoted improvement of the skin condition. This improvement resulted without the irratation and peeling normally associated with prior art acne treatment compositions, and specifically, those compositions intended for topical application.

For example, Kligman et al [Arch. Derm. 99:469 (1969)] reported successful use of the composition containing retinoic (vitamin A) acid in the topical treatment of acne. Success was attributed to the irritating properties and "peeling" ability.

In addition, British Pat. No. 901,659 (July 25, 1962) describes the use of resorcinol, vatamin A, or its derivatives and a polyalkylene glycol in the treatment of acne. The polyalkylene glycol is present to prevent irritation caused by resorcinol.

We have now discovered, however, that actinic and nonactinic keratoses may be successfully treated without skin irritation by utilizing retinal. When used as a topical agent the therapeutic dose of this vitamin A aldehyde in cream, ointment or solution may vary from 0.01 to 2 percent by weight.

We have established through extensive tests on humans having keratoses that topical application of either a cream or ointment or solution containing from 0.01 to 2 percent and preferably from 0.02 to 0.5 percent of retinal is effective when applied on a daily basis to eradicate, usually within three to eight weeks time, keratotic lesions and to restore the affected areas to a normal skin appearance or at least to a state of substantial improvement thereof without additional skin irritation.

Accordingly, it is the object of this invention to provide a relatively nontoxic, nonallergenic medicinal composition which when topically applied will reliably eradicate or improve the symptoms and signs of keratoses.

It is another object to provide a method for treating keratoses with a nonirritating and nontoxic cream, ointment or solution containing retinal.

It is still another object to provide a safe and efficient method for treating the symptoms of keratoses through regular topical application of a medicinal composition containing retinal which will promote healing within about 3 to 8 weeks.

Specifically, the compound of this invention found to be useful in the treatment of keratoses is retinal present in a vehicle in a concentration of from 0.01 percent to 2 percent, by weight.

PREPARATION OF THE THERAPEUTIC COMPOSITIONS

Retinal has six representative stereoisomers: namely all-trans; 13-cis; 11-cis; 9-cis; 11,13-di-cis and 9,13-di-cis. The most commonly used vitamin aldehyde, however, is all-trans retinal.

Commercially available all-trans retinal (hereinafter referred to as retinal) is in a form of yellowish crystals. To prepare a therapeutic composition retinal is first dissolved in ethanol, isopropylmyristate, isopropyl palmitate or mineral oil. A solution thus prepared may be admixed in a conventional manner with any commonly available lotion, cream or ointment.

The concentration of retinal ranges from 0.01 to 2% by weight of the total composition. The preferred concentration range, however, is from 0.02 to 0.5%.

The ethanol, isopropyl myristate, isopropyl palmitate or mineral oil used to dissolve retinal according to this invention may range in concentration of from 5 to 50% by volume of the total composition. The preferred concentration, thereof, however, is 5 to 20%.

When a therapeutic composition is prepared in a solution form, retinal is first dissolved in ethanol, and water, propylene glycol or 1,3-butanediol may be added to the alcoholic solution. The ratio of each vehicle may vary; however, the preferred concentration of each vehicle should not exceed 50% by volume of the total composition.

It has been found that the therapeutic compositions of this invention, prepared as above, may be stored in brown plastic or glass bottles or jars at room temperature for extended periods of time without change in the therapeutic efficaciousness.

The following are illustrative examples of formulating compositions according to this invention. Although the examples utilize only selected forms of the formulations, useful according to this invention, it should be understood that the following examples are illustrative and not limiting.

EXAMPLE 1

Retinal 0.1g was dissolved in 40 ml of ethanol. After all the crystals had been solubilized 40 ml of water and 20 ml of propylene glycol were added to the alcoholic solution. The light yellowish solution thus prepared consisted of 0.1% active ingredient.

EXAMPLE 2

Retinal 0.05g was dissolved in 50 ml of ethanol. The solution was admixed with 30 ml of water and 20 ml of 1, 3-butanediol to make a composition containing 0.05% by weight of the vitamin A aldehyde.

EXAMPLE 3

Retinal 0.05g was dissolved in 40 ml of mineral oil, and the solution was admixed with 60g of water-in-oil ointment prepared from mineral oil, petrolatum, spermaceti and water with a surfactant such as sorbitan sesquioleate. The ingredients of the water-in-oil ointment were present in 10:10:6:68:6 parts by weight respectively. The water-in-oil lotion thus prepared consisted of 0.05% active ingredient.

EXAMPLE 4

Retinal 0.1g was dissolved in 10 ml of isopropyl myristate and the solution was admixed with 90g of USP grade hydrophilic ointment to a uniform consistency. The water-washable cream thus prepared consisted of 0.1% active ingredient.

EXAMPLE 5

Retinal 0.2g was dissolved in 15 ml of isopropyl palmitate, and the solution was admixed with 85g of water-in-oil ointment prepared from mineral oil, petrolatum, spermaceti and water with a surfactant such as sorbitan sesquioleate. The ingredients of said water-in-oil ointment were present in 10:10:6:68:6 parts by weight respectively. The water-nonwashable ointment thus prepared consisted of 0.2% active ingredient.

EXAMPLE 6

Retinal 0.1g was dissolved in 40 ml of mineral oil, and the solution was admixed with 60g of USP grade white petrolatum to a uniform consistency. The water free ointment thus prepared consisted of 0.1% active ingredient.

TEST RESULTS

A total of 11 patients having actinic or nonactinic keratoses were selected for this study. Each patient was instructed to apply a test composition, prepared according to Example 4, topically twice daily on the lesions. Standardized color photos were taken of the skin lesions prior to initiating the treatment and after 4 to 8 weeks of topical treatment with the test cream. The test results were determined both by clinical impression and also by comparison of the photos before and after treatment. A total of 8 patients showed substantial reduction in the number of keratotic lesions after four weeks of topical treatment, and complete resolution of most lesions after eight weeks of topical treatment. In the remaining three patients, partial resolution of keratoses had occurred within the eight week interval and required more prolonged topical therapy to cause more complete resolution of lesions.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced herein.

What is claimed and desired to be secured by Unites States Letters Patent is:

1. A method of treating actinic or nonactinic keratoses in humans having skin affected thereby without irritating the skin comprising:
    administering topically to the affected skin a therapeutically effective amount of a composition comprising retinal in a pharmacologically acceptable vehicle, on a daily basis to eradicate actinic or nonactinic keratotic lesions.

2. The method of claim 1 wherein retinal is present in from 0.01 to 2.0 percent by weight of said composition.

3. The method of claim 1 wherein retinal is present in 0.02 to 0.5 percent weight of said composition.

4. The method of claim 1 wherein said vehicle comprises a retinal solvent selected from the group consisting of ethanol, isopropyl myristate, isopropyl palmitate, and mineral oil.

5. The method of claim 4 wherein said solvent is present in a concentration of from 5 to 50%, by volume, of the total composition.

6. The method of claim 4 wherein said solvent is present in a concentration of from 5 to 20%, by volume, of the total composition.

7. The method of claim 4 wherein said vehicle further comprises a member selected from the group consisting of water, propylene, glycol, and 1,3-butanediol.

8. The method of claim 7 wherein said member is present in a concentration of no more than about 50% by volume of the total composition.

* * * * *